United States Patent
Chiuh et al.

(10) Patent No.: US 12,251,409 B2
(45) Date of Patent: Mar. 18, 2025

(54) USE OF CYANOBACTERIAL BIOMASS IN TREATING HEPATITIS B VIRUS INFECTION

(71) Applicant: FAR EAST BIO-TEC CO., LTD., Taipei (TW)

(72) Inventors: Chuang-Chun Chiuh, Taipei (TW); Yi-Hsiang Chen, Taipei (TW); Ming-Shun Wu, Taipei (TW); Chun-Wei Cheh, Taipei (TW)

(73) Assignee: FAR EAST BIO-TEC CO., LTD., Taipei (TW)

( * ) Notice: Subject to any disclaimer, the term of this patent is extended or adjusted under 35 U.S.C. 154(b) by 644 days.

(21) Appl. No.: 16/875,474

(22) Filed: May 15, 2020

(65) Prior Publication Data

US 2020/0276251 A1 Sep. 3, 2020

Related U.S. Application Data

(63) Continuation of application No. PCT/US2018/061613, filed on Nov. 16, 2018.

(60) Provisional application No. 62/587,488, filed on Nov. 17, 2017.

(51) Int. Cl.
| | |
|---|---|
| *A61K 35/748* | (2015.01) |
| *A61K 9/20* | (2006.01) |
| *A61K 38/21* | (2006.01) |
| *A61K 45/06* | (2006.01) |
| *A61P 1/16* | (2006.01) |
| *A61P 43/00* | (2006.01) |

(52) U.S. Cl.
CPC .......... *A61K 35/748* (2013.01); *A61K 9/2095* (2013.01); *A61K 38/212* (2013.01); *A61P 1/16* (2018.01); *A61P 43/00* (2018.01); *A61K 45/06* (2013.01)

(58) Field of Classification Search
CPC .. A61K 35/748; A61K 9/2095; A61K 38/212; A61K 45/06; A61P 43/00; A61P 1/16
See application file for complete search history.

(56) References Cited

PUBLICATIONS

Ming Shun Wu (U.S. National Library of Medicine ClinicalTrials.gov retrieved from https://www.clinicaltrials.gov/ct2/show/study/NCT02953600).*

Shaw et al. (Expert Rev. Anti Infect. Ther. vol. 2 No. 6, pp. 853-871).*

Man-Fung Yuen et al., "HbsAg Seroclearance in Chronic Hepatitis B in Asian Patients: Replicative Level and Risk of Hepatoceelular Carcinoma", Gastroenterology, Oct. 2008; 135, pp. 1192-1199, Department of Medicine, The University of Hong Kong, Queen Mary Hospital, Hong Kong; and Dept. of Pathology, The University of Hong Kong, Queen Mary Hosptial, Hong Kong.

Anna S. Lok et al., "Hepatitis B cure: From discovery to regulatory approval", EASL Journal of Hepatology, vol. 67, 2017, pp. 847-861,.

* cited by examiner

Primary Examiner — Robert A Zeman
(74) Attorney, Agent, or Firm — MUNCY, GEISSLER, OLDS & LOWE, P.C.

(57) ABSTRACT

Disclosed herein is the use a cyanobacterial biomass for treating hepatitis B virus (HBV) infection, in particular, chronic HBV infection. According to various embodiments of the present disclosure, the cyanobacterial biomass, upon administration of at least one month, significantly reduces the level of the surface antigen of hepatitis B virus (HBsAg) detectable in the subject receiving the treatment and/or mitigates insomnia associated with chronic HBV infection.

8 Claims, 1 Drawing Sheet
Specification includes a Sequence Listing.

SEQUENCE LISTING

```
<160> NUMBER OF SEQ ID NOS: 1

<210> SEQ ID NO 1
<211> LENGTH: 2036
<212> TYPE: DNA
<213> ORGANISM: Arthrospira maxima

<400> SEQUENCE: 1
gctcaggatg aacgctggcg gtctgcttaa cacatgcaag tcgaacgggc tcttcggagc      60
tagtggcgga cgggtgagta acacgtgaga atctggctcc cggtcgggga caacagaggg     120
aaacttctgc taatcccgga tgagccgaaa ggtaaaagat ttatcgccgg gagatgagct     180
cgcgtctgat tagctagttg gtgaggtaaa ggctcaccaa ggcgacgatc agtagctggt     240
ctgagaggat gatcagccac actgggactg agacacggcc cagactccta cgggaggcag     300
cagtggggaa ttttccgcaa tgggcgcaag cctgacggag caagaccgcg tggggagga     360 aggctcttgg gttgtaaacc ccttttctca aggaagaaca caatgacggt acttgaggaa     420
taagcctcgg ctaactccgt gccagcagcc gcggtaatac ggaggaggca agcgttatcc     480
ggaatgattg ggcgtaaagc gtccgtaggt ggctgttcaa gtctgctgtc aaagacagtg     540
gcttaactac tgaaaggcag tggaaactga acagctagat tacggtaggg gcagagggaa     600
ttcccggtgt agcggtgaaa tgcgtagata tcgggaagaa caccggtggc gaaagcgctc     660
tgctgggccg taactgacac tgagggacga aagctagggg agcgaatggg attagatacc     720
ccagtagtcc tagccgtaaa cgatggaaac taggtgtagc ctgtatcgac ccgggctgtg     780
ccgaagctaa cgcgttaagt ttcccgcctg gggagtacgc acgcaagtgt gaaactcaaa     840
ggaattgacg ggggcccgca caagcggtgg agtatgtggt ttaattcgat gcaacgcgaa     900
gaaccttacc agggcttgac atgtccggaa tcttggtgaa agccgagagt gccttcggga     960
gccggaacac aggtggtgca tggctgtcgt cagctcgtgt cgtgagatgt tgggttaagt    1020
cccgcaacga gcgcaaccct cgtccttagt tgccatcatt cagttgggca ctttaggag     1080 actgccggtg acaaaccgga ggaaggtggg gatgacgtca agtcatcatg ccccttacgt    1140
cctgggctac acacgtacta caatgggggg gacaaaggga gccaagacg cgagtctgag     1200 ccaatcccgt aaacctctcc tcagttcaga ttgcaggctg caactcgcct gcatgaagga    1260
ggaatcgcta gtaatcgcag gtcagcatac tgcggtgaat ccgttcccgg gccttgtaca    1320
caccgcccgt cacaccatgg aagttagcca cgcccgaagt cgttactcta accgttcgcg    1380
gaggaggatg ccgaaggcag ggctgatgac tggggtgaag tcgtaacaag gtagccgtac    1440
```

-continued

```
cggaaggtgt ggctggatca cctccttttt agggagacct acttcaggac atcgtgcgat   1500
gataataata gccgagtctt gaggtcatcc ttaggtcgga tggggcggtc agagagcttt   1560
caaactttag ggttcgtgtt atgggctatt agctcaggtg gttagagcgc acccctgata   1620
agggtgaggt ccctggttca agtccaggat ggcccacatc caccccaaac tgggggtata   1680
gctcagttgg tagagcgctg cctttgcacg gcagaagtca gcggttcgag tccgcttacc   1740
tccactctcc tagaattagg tgctagttgg ggtgaggtag tcttgaattg agaaattgag   1800
agttggtgac tgtacagctc ctaagtctgt agatgttaat ctaggactag atagctggac   1860
ataagttcca gtcagaacct tgaaaactgc atagagaaaa gcataatggt gtaggaaaac   1920
gtcgtaaaga caattccaat gtaggtcaag ctacaaaggg ctaacggtgg attcctaggc   1980
acacagaggc gatgaaggac gtggcgaccc acgaaaggct tcggggagct ggaagc       2036
```

USE OF CYANOBACTERIAL BIOMASS IN TREATING HEPATITIS B VIRUS INFECTION

CROSS-REFERENCE TO RELATED APPLICATIONS

This application is a continuation application of International Patent Application No. PCT/US2018/061613, filed Nov. 16, 2018, which relates to and claims the benefit of U.S. Provisional Application No. 62/587,488, filed Nov. 17, 2017, the content of which is incorporated herein by reference in their entirety.

BACKGROUND OF THE INVENTION

1. Field of the Invention

The present disclosure, in general, relates to the field of treating hepatitis B virus (HBV) infection. More particularly, the present disclosure relates to the use of a cyanobacterial biomass in the treatment of HBV infection.

2. Description of Related Art

HBV is a small, double-shelled virus in the family Hepadnaviridae. It may cause both acute and chronic infections. The acute infection with HBV is associated with acute viral hepatitis, an illness characterized by malaise, nausea, vomiting, headache, fever, skin rashes, arthralgia, arthritis, myalgia and/or dark urine, before the onset of jaundice. The illness may last for a few weeks and gradually improves in most affected people, in which only about 1 to 2% of acutely infected people develop into fulminant hepatic failure (ALF).

The proportion of patients having acute HBV infection and then progressing to the chronic infection usually varies with age and immune status. It has been reported that about 90% of infants who acquire HBV infection from their mothers at birth or in infancy become chronically infected. Of children who are infected by HBV between 1 year and 5 years of age, 30% to 50% become chronically infected. By adulthood, the risk of acquiring chronic HBV infection is approximately 5%, in which the immune-compromised or deficient patients are more predisposed to develop the chronic HBV infection as compared to the immune-competent adults. The chronic infection is responsible for most HBV-related morbidity and mortality, including chronic hepatitis, cirrhosis, liver failure, and hepatocellular carcinoma.

The diagnosis of HBV infection is usually made on the basis of serological tests for HBV antigen and antibodies. HBV contains numerous antigenic components, including hepatitis B surface antigen (HBsAg), hepatitis B core antigen (HBcAg), and hepatitis B e antigen (HBeAg), in which the HBsAg, a protein associated with the replication and infectivity of HBV, is the most commonly used marker for diagnosing HBV infection. In general, HBsAg can be identified in the serum 30 to 60 days post-infection and persist for variable periods. Antibody to HBsAg (anti-HBs or HBsAb) usually develops during convalescence after HBV infection that neutralizes HBV infectivity and clears the circulating HBsAg and the infectious HBV particles from the peripheral blood. Persistence of HBsAg for more than 6 months in duration indicates the development of either a chronic carrier state or chronic HBV infection.

Currently, there are two major categories of anti-viral treatment that have been approved for the treatment of chronic HBV infection in many countries: the first one being interferon alpha (IFN-α) or pegylated IFN-α (PEG-IFNα), while the second one includes various nucleoside or nucleotide analogs (e.g., lamivudine, adefovir, entecavir telbivudine, and tenofovir). However, these drugs merely stop or decrease the viral replication, none of which are capable of clearing the infection. Accordingly, the majority of patients suffering from chronic HBV infection require prolonged treatment to continuously suppress the viral replication.

In view of the foregoing, there exists in the related art a need for a novel drug useful in the treatment of chronic HBV infection.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

In one aspect, the present disclosure is directed to a method for treating an infection caused by the Hepatitis B virus (HBV), in a subject in need thereof. As embodied and broadly described herein, the present treatment method is effective in treating HBV infection; including, chronic HBV infection. Also, the present method is effective in lowering the surface antigen of hepatitis B virus (HBsAg) detectable in the subject, and in some cases, results in a seroclearance of HBsAg. Moreover, the present method is also effective in preventing or delaying the onset of liver diseases (e.g., liver fibrosis, cirrhosis or hepatic decompensation) associated with chronic HBV infection. Further, the present method can effectively mitigate insomnia associated with chronic HBV infection.

According to some embodiments of the present disclosure, the method comprises the step of administering to the subject an effective amount of a cyanobacterial biomass.

According to certain embodiments of the present disclosure, the cyanobacterial biomass is derived from *Arthrospira maxima*.

In various embodiments, the subject is a mammal, including human.

In some embodiments, the subject suffers from chronic HBV infection. In some other embodiments, the subject suffers from liver cirrhosis or hepatic decompensation associated with chronic HBV infection. In still some other embodiments, the subject suffers from insomnia associated with chronic HBV infection. In some other embodiments, the subject suffers from liver fibrosis associated with chronic HBV infection.

In optional embodiments, the effective amount is 1 to 1,000 mg/Kg body weight per day; preferably, 20-200 mg/Kg body weight per day. Still optionally, the effective amount is 1 to 20 grams per day. According to yet another embodiment, the cyanobacterial biomass is administered orally.

According to some embodiments of the present disclosure, the cyanobacterial biomass is administered daily for at least one month. Optionally, the cyanobacterial biomass is administered daily for at least six months.

In some optional embodiments, the method for treating the HBV infection further comprises the step of administering an effective amount of an antiviral agent, such as an interferon alpha (IFN-α), pegylated IFN-α, nucleoside analog, or nucleotide analog. Illustrative examples of nucleoside or nucleotide analogs include, but are not limited to, acyclovir, famciclovir, ganciclovir, valacyclovir, vidarabine, ribavirin, zoster-immune globulin (ZIG), lamivudine, adefovir, dipivoxil, entecavir, telbivudine, clevudine, and tenofovir.

According to certain embodiments of the present disclosure, the subject suffers from chronic HBV infection, and the cyanobacterial biomass is administered for at least one month to reduce the level of the surface antigen of hepatitis B virus (HBsAg) detectable in the subject.

According to some other embodiments of the present disclosure, the subject suffers from insomnia associated with chronic HBV infection, and the cyanobacterial biomass is administered for at least three months to mitigate insomnia.

According to some other embodiments of the present disclosure, the subject suffers from liver fibrosis associated with chronic HBV infection, and the cyanobacterial biomass is administered for at least three months to mitigate liver fibrosis. According to some other embodiments of the present disclosure, the subject suffers from liver diseases (e.g., liver cirrhosis or hepatic decompensation) associated with chronic HBV infection or is predisposed to liver diseases due to chronic HBV infection, and the cyanobacterial biomass is administered for at least one month to prevent or delay the onset of liver diseases.

In still another aspect, the present disclosure is directed to a pharmaceutical or nutraceutical composition for treating HBV infection, including chronic HBV infection. Subject matters that are also included in other aspects of the present disclosure include the use of a cyanobacterial biomass in the manufacture of a medicament or nutraceutical composition for use in the treatment of HBV infection, including chronic HBV infection.

The pharmaceutical or nutraceutical composition is also useful in treating insomnia or liver d associated with chronic HBC infection. In some embodiments, the administration of the present pharmaceutical or nutraceutical composition effectively lowers the HBsAg level of the subject, and may even result in the seroclearance of HBsAg in some subjects.

According to some embodiments, the pharmaceutical or nutraceutical composition comprises an effective amount of a cyanobacterial biomass and a pharmaceutically or nutraceutically acceptable excipient.

According to certain embodiments of the present disclosure, the cyanobacterial biomass is derived from *Arthrospira maxima*.

In some embodiments, the pharmaceutical or nutraceutical composition is formulated into a preparation suitable for oral administration, such as a tablet, caplet, capsule or a liquid dosage form (e.g., a dispersion or suspension). According to some embodiments, the pharmaceutical or nutraceutical composition is formulated as a tablet, and the pharmaceutically or nutraceutically acceptable excipient is silicon dioxide or a sucrose ester of fatty acid.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

Figure 1:
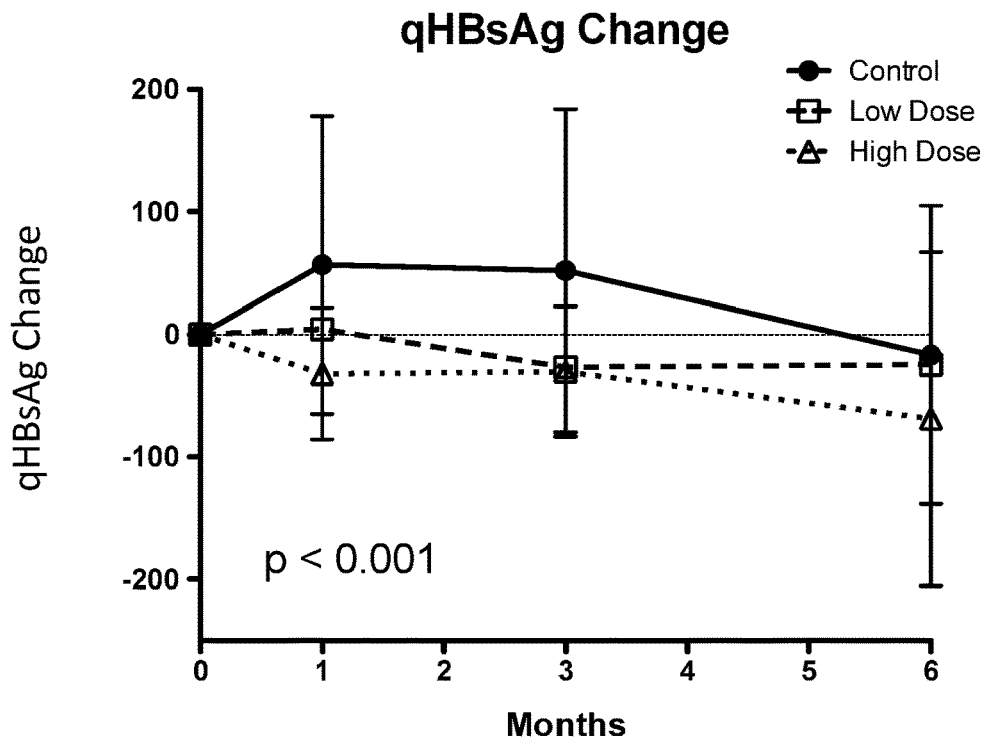
FIG. 1 is a line chart depicting the qHBsAg change of subjects treated with specified treatments.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values, and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The term "nucleoside analog" or "nucleotide analog" as used herein refers to a molecule, which is similar to a nucleoside or a nucleotide, and is capable of performing at least some of the biochemical functions of the nucleoside or the nucleotide. Specifically, the term "nucleotide analog" refers to a molecule that is structurally similar to a natural nucleotide and that can function in a similar manner as the naturally occurring nucleotide (e.g., exhibits similar ability to base pair with one of the naturally occurring bases). The term "nucleoside analog" as used herein refers to a molecule that is structurally similar to a natural nucleoside and that can function in a similar manner as the naturally occurring nucleoside (e.g., exhibits similar ability to be incorporated into DNA by DNA replication).

The terms "treatment" and "treating" as used herein may refer to a preventative (e.g., prophylactic), curative or palliative measure. In particular, the term "treating" as used herein refers to the application or administration of the present cyanobacterial biomass or a pharmaceutical or nutraceutical composition comprising the same to a subject, who has a medical condition (that is, HBV infection or chronic HBV infection), a symptom (e.g., insomnia, fatigue, malaise, myalgia, arthralgia) associated with the medical condition, a disease or disorder (e.g., liver cirrhosis or hepatic decompensation) secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. The treatment may be administered to a subject who does not exhibit signs of a disease, disorder, and/or condition, and/or to a subject who exhibits only early signs of a disease, disorder and/or condition, for the purpose of decreasing the risk of developing pathology associated with the disease, disorder and/or condition. In preferred embodiments, the present cyanobacterial biomass can be used to ameliorate or prevent insomnia or liver cirrhosis in vivo. Also, the administration of the present cyanobacterial biomass results in a seroclearance of the HBsAg in the subject. Accordingly, the present treatment method provides means for substantially eradicating the infectious pathogens in the host organism such that the pathogen is not-detectable in the host organism.

The terms "subject" and "patient" are used interchangeably herein and are intended to mean an animal including the human species that is treatable by the present cyanobacterial biomass, pharmaceutical or nutraceutical composition, and/or method of the present invention. The term "subject" or "patient" intended to refer to both the male and female gender unless one gender is specifically indicated.

The terms "application" and "administration" are used interchangeably herein to mean the application of the present cyanobacterial biomass or a pharmaceutical or nutraceutical composition of the present invention to a subject in need of a treatment thereof. For example, the subject may be someone having or suspected of having chronic HBV infection.

The term "effective amount" as used herein refers to the quantity of the present cyanobacterial biomass that is sufficient to yield a desired therapeutic response. For therapeutic purposes, the effective amount is also one in which any toxic or detrimental effects of the component are outweighed by the therapeutically beneficial effects. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two, or more doses in a suitable form to be administered at one, two or more times throughout a designated time period. The specific effective or sufficient amount will vary with such factors as particular condition being treated, the physical condition of the patient (e.g., the patient's body mass, age, or gender), the type of mammal or animal being treated, the duration of the treatment, the nature of concurrent therapy (if any), and the specific formulations employed and the structure of the active component or its derivatives. The effective amount may be expressed, for example, as the total mass of cyanobacterial biomass (e.g., in grams, milligrams or micrograms) or a ratio of the mass of the cyanobacterial biomass to the body mass, e.g., as milligrams per kilogram (mg/kg). Alternatively, the effective amount can be expressed in the concentration of the active component (e.g., the cyanobacterial biomass of the present disclosure), such as molar concentration, mass concentration, volume concentration, molality, mole fraction, mass fraction and mixing ratio.

The phrase "nutraceutically- or pharmaceutically-acceptable excipient" as used herein means a material, composition or vehicle, such as a liquid or solid filler, diluent, carrier, solvent or encapsulating material, involved in carrying or transporting the subject agents from one organ, or portion of the body, to another organ, or portion of the body. Each excipient must be "acceptable" in the sense of being compatible with the other ingredients of the formulation. The nutraceutical or pharmaceutical formulation contains the cyanobacterial biomass of the invention in combination with one or more nutraceutically- or pharmaceutically-acceptable ingredients. The excipient can be in the form of a solid, semi-solid or liquid diluent, cream or a capsule. These nutraceutical or pharmaceutical preparations are a further object of the invention. Usually, the amount of the cyanobacterial biomass is between 0.1-95% by weight of the preparation, preferably between 0.2-20% by weight in preparations for parenteral use and preferably between 1 and 50% by weight in preparations for oral administration. For the clinical use of the methods of the present invention, the nutraceutical or pharmaceutical composition of the invention is formulated into formulations suitable for the intended route of administration, such as oral administration.

As used here the term "biomass" is meant biomass derived from a culture containing *A. maxima*. This term includes the living and dead organisms, as well as a ready-made, dried, frozen or otherwise previously worked biomass.

Spontaneous HBsAg seroclearance is a rare event in the chronic HBV infection. Prior researches indicate an annual incidence of spontaneous HBsAg seroclearance ranges from about 0.1 to 2.5% in various countries. Patients suffering from chronic HBV infection have to take antiviral medications continuously to inhibit the replication of HBV virus within the patient's body. At the early stage of the antiviral treatment, the antiviral medications may effectively lower the HBsAg level detectable in the patients (the level may vary from patient to patient depending on a wide variety of factors); however, the HBsAg level would remain constant during the subsequent treatment and it is often very difficult to further lower the HBsAg level in the patient with the currently available antiviral treatments after the HBsAg level has reached the individual constant level.

The present disclosure is based, at least in part, on the discovery that the present cyanobacterial biomass, upon oral administration for an extended period (e.g., at least one month) together with an antiviral agent, is capable of further lowering the HBsAg level in the subject, with the possibility of achieving the seroclearance of HBsAg in patients suffering from chronic HBV infections. By lowering the HBsAg level and even clearing the HBsAg in the sera of the patient, it is possible to reduce the patient's risk in developing liver cirrhosis, hepatic decompensation, and/or hepatocellular carcinoma. In view of the foregoing, the present disclosure proposes methods for treating HBV infections, including the chronic HBV infection. Some embodiments of the present disclosure are directed to methods for treating symptoms or disorders associated with, secondary to, or caused by such HBV infection. Also provided herein is the use of said cyanobacterial biomass for use in the treatment of said HBV infection, as well as for use in the manufacture of a medicament or nutraceutical preparation for said treatment purpose. The medicament (i.e., a pharmaceutical composition) or the nutraceutical preparation is, of course, a subject matter covered by the scope of the present application.

In one aspect, the present disclosure is directed to a method for treating an infection caused by HBV or a symptom or disorder associated with, secondary to, or caused by said HBV infection, in a subject in need thereof.

Cyanobacteria are microscopic bacteria found in land and fresh, brackish, or marine water. Cyanobacteria carry out oxygenic photosynthesis. Because they are photosynthetic, aquatic cyanobacteria are commonly referred to as bluegreen algae. Currently, there are more than 2,000 described species under the cyanobacteria phylum. Cyanobacteria have been identified as a rich source of biologically active compounds with antiviral, antibacterial, antifungal and anticancer activities. Isolated compounds from cyanobacteria belong to groups of polyketides, amides, alkaloids, fatty acids, indoles, and lipopeptides. Efforts are being made to identify active extract fractions or compounds with desired therapeutic effects.

*Spirulina* refers to the dietary supplement made from the dried biomass of *Arthrospira platensis* and *A. maxima. A. maxima* (or *Spirulina maxima*) are found in tropical or subtropical areas with salty and alkali water bodies. For example, it is common in Lake Chad, Africa, and Lake Texcoco, Mexico. These two species were once classified in the genus *Spirulina*. Although according to the current taxonomy, the name *Spirulina* for these two strains is inappropriate, and agreement exists that the genus *Arthrospira* includes *A. platensis* and *A. maxima*, the outdated taxonomy is still used today, and the dietary supplements made therefrom are most often referred to by their popular name, *spirulina*. *Spirulina* has been used as a food source since ancient Aztec times. Nonetheless, the present invention is the first to discover its capability in further reducing the HBsAg level in subjects suffering from chronic HBV infection, and apply this discovery into a practical use.

According to certain embodiments of the present disclosure, the cyanobacterial biomass is derived from *Arthrospira maxima*. According to yet another embodiment, the cyanobacterial biomass is administered orally. According to some embodiments of the present disclosure, the cyanobacterial biomass is provided as a dried powder; however, the present disclosure is not limited thereto. Alternatively, the dried powdered may be further processed into a tablet, caplet or capsule. Still alternatively, the cyanobacterial biomass may be formulated into a liquid preparation, such as a dispersion or suspension having an effective amount of the cyanobacterial biomass.

In various embodiments, the subject is a mammal, which may benefit from the treatment method of the present disclosure. As used herein, "mammal" refers to all members of the class Mammalia, including humans; primates (e.g., monkey and chimpanzee); domestic and farm animals, such as dog, cat, rabbit, pig, sheep, goat, cow, horse, and cattle; as well as zoo, sports or pet animals; and rodents, such as mouse, rat and guinea pig. In an exemplary embodiment, the patient is a human.

In some embodiments, the subject suffers from chronic HBV infection. A patient suffering from chronic HBV infection has a higher risk in developing liver cirrhosis, and the administration of the cyanobacterial biomass to such patient may reduce the patient's risk in developing the liver diseases (e.g., liver cirrhosis or hepatic decompensation). In some other embodiments, the subject suffers from liver cirrhosis associated with chronic HBV infection, and the cyanobacterial biomass is administered for a period (e.g., at least one month) sufficient to inhibit or delay the progression of the liver cirrhosis.

It has been reported that the patients having progressive liver disease (e.g., liver cirrhosis and hepatic decompensation etc.) usually present with disturbed sleep patterns (e.g., insomnia). In still some other embodiments, the subject suffers from insomnia or disturbed sleep patterns associated with chronic HBV infection, and the cyanobacterial biomass is administered to mitigate insomnia and improve the sleeping quality of the subject. In some embodiments, the cyanobacterial biomass is administered to a patient suffering from chronic HBV infection to lower the patient's risk in developing hepatocellular carcinoma. In view of the foregoing, the present method involving the administration of the cyanobacterial biomass to patients suffering from HBV or chronic HBV infection can be used as a therapeutic measure, preventive measure, or for nutraceutical purposes.

In optional embodiments, the effective amount of the cyanobacterial biomass is about 1 to 1,000 mg/Kg body weight per day; preferably, about 20-200 mg/Kg body weight per day; more preferably, about 40 to 120 mg/Kg body weight per day. For example, the effective amount may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1,000 mg/Kg body weight per day. Still optionally, the effective amount is 1 to 20 grams per day, such as 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or 20 grams per day. According to some other embodiments, the cyanobacterial biomass is administered once, twice, or three times a day.

According to some embodiments of the present disclosure, the cyanobacterial biomass is administered daily for at least one month. Optionally, the cyanobacterial biomass is administered daily for at least six months. Still optionally, the cyanobacterial biomass is administered daily for at least nine months or even over a year. According to certain embodiments of the present disclosure, the cyanobacterial biomass is administered to the subject daily for at least 1, 2, 3, 4, 5, 6, 7, 8, 9, 10, 11, 12, 13, 14, 15, 16, 17, 18, 19, 20, 21, 22, 23, 24 or more months. As could be appreciated, since the cyanobacterial biomass has long been used as the dietary supplement, the safety regarding the long-term administration of cyanobacterial biomass has been recognized. Therefore, the cyanobacterial biomass may be used for therapeutic, preventive or nutraceutical purposes for a longer period without raising substantial safety issues.

In some optional embodiments, the method for treating the HBV infection further comprises the step of administering an effective amount of an antiviral agent, such as an interferon alpha (IFN-α), pegylated IFN-α, nucleoside analog, or nucleotide analog. Illustrative examples of nucleoside or nucleotide analogs include, but are not limited to, acyclovir, famciclovir, ganciclovir, valacyclovir, vidarabine, ribavirin, zoster-immune globulin (ZIG), lamivudine, adefovir, dipivoxil, entecavir, telbivudine, clevudine, and tenofovir. Alternatively, the anti-viral agent may be (1) a small interfering RNA (siRNA) that interferes and/or inhibits the replication of HBV, (2) a molecular interfering and/or inhibiting the entry of HBV into liver cells (e.g., myrcludex B), (3) a molecular that interferes and/or inhibits the formation of viral capsid (e.g., morphothiadin (GLS4), NVR 3-778, JNJ56136379 and AB-423 etc.), or (4) a molecule interfering and/or inhibiting the production or expression of viral antigen (e.g., Rep 2139, Rep 2165, and RO7020322 (RG7834) etc.). The cyanobacterial biomass may be administered prior to, concurrent with, or after the administration of the antiviral agent. Alternatively, the cyanobacterial biomass and the antiviral may have different dosing regimen so that the two are taken at different time intervals during the course of treatment.

In still another aspect, the present disclosure is directed to a pharmaceutical or nutraceutical composition for treating HBV or chronic HBV infection. According to various embodiments, the pharmaceutical or nutraceutical composition is also useful in treating or preventing insomnia or liver cirrhosis associated with chronic HBC infection. According to optional embodiments, the pharmaceutical or nutraceutical composition may also be used in reducing the patient's risk in developing hepatocellular carcinoma. In some embodiments, the co-administration of the present pharmaceutical or nutraceutical composition with an antiviral agent effectively lowers the HBsAg level of the subject, as compared with patients receiving only the antiviral agent. The long-term administration of the present pharmaceutical or nutraceutical composition is expected to result in the seroclearance of HBsAg in some subjects.

According to some embodiments, the pharmaceutical or nutraceutical composition comprises an effective amount of a cyanobacterial biomass (e.g., died biomass from *A. maxima*) and a pharmaceutically or nutraceutically acceptable excipient.

In some embodiments, the pharmaceutical or nutraceutical composition is formulated into a preparation suitable for oral administration, such as a solid dosage form (e.g., capsules, sachets, tablets, pills, lozenges, powders or granules) and a liquid dosage form (e.g., a solution, suspension, emulsion, microemulsion, or dispersion).

Any of the described solid dosage forms may optionally contain coatings and shells, such as enteric coatings, and coatings for modifying the release rate of any of the ingredients. Examples of such coatings are well known in the art. In one example, the pharmaceutical compositions of this disclosure are tablets such as quick-release tablets. In still another example, the pharmaceutical compositions of this disclosure are formulated into sustained release forms. In another example, the pharmaceutical compositions of this disclosure are powders that are encapsulated in soft and hard gelatin capsules.

Depending on desired purposes, the pharmaceutically or nutraceutically acceptable excipient of the present pharmaceutical composition may be a water-soluble excipient or a water-insoluble excipient. Exemplary water-soluble excipients include, but are not limited to, mannitol, lactose, sucrose, glucose, maltose, hydrogenated maltose, maltotetraose, fructose, lactulose, lactitol, sorbitol, maltitol, erythritol, xylitol and a combination thereof. Examples of water-insoluble excipients include, but are not limited to, cellulose derivatives, microcrystalline cellulose, ethylcellulose, silicon dioxide, crospovidone, sodium starch glycolate, cros- carmellose sodium, methacrylate polymers, corn starch, dibutyl phthalate, diethyl phthalate, dibutyl sebacate, triacetin and a combination thereof.

The liquid formulation may further include a buffering agent to maintain the desired pH. The liquid dosage formulations may also be filled into soft gelatin capsules.

Preferably, the pharmaceutically or nutraceutically acceptable excipient is incorporated in the composition in an amount of about 0.01% to about 85% (e.g., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84 or 85%) by weight, preferably about 0.01% to about 50% by weight, more preferably about 0.01% to about 10% by weight on the basis of the total weight of the composition.

According to one specific example of the present disclosure, the pharmaceutically or nutraceutically acceptable excipient is silicon dioxide or a sucrose ester of fatty acid that is incorporated in the present pharmaceutical or nutraceutical composition in an amount of about 0.01% to 10% by weight on the basis of the total weight of the composition.

Compositions of the present invention can also comprise various additives known to those skilled in the art. For example, solvents, including relatively small amounts of alcohol, may be used to solubilize certain active ingredients. Other optional pharmaceutically or nutraceutically acceptable additives include opacifiers, antioxidants, fragrance, colorant, gelling agents, thickening agents, stabilizers, surfactants, and the like. Other agents may also be added, such as antimicrobial agents, to prevent spoilage upon storage, i.e., to inhibit the growth of microbes such as yeasts and molds. Permeation enhancers and/or irritation-mitigating additives may also be included in the composition of the present invention. Other examples include solvents, dispersion media, coatings, surfactants, antioxidants, preservatives (e.g., antibacterial agents, antifungal agents), isotonic agents, absorption delaying agents, stabilizers, gels, binders, excipients, disintegration agents, lubricants, sweetening agents, flavoring agents, dyes, such like materials and combinations thereof, as would be known to one of ordinary skill in the art.

The present composition comprising the present cyanobacterial biomass may be formulated as dietary supplements, which may further comprise one or more additional nutritional components, such as vitamins, minerals, fiber, fatty acids, or amino acids. Alternatively, the dietary supplements may comprise one or more edible carriers, which may confer one or more of the benefits to the cyanobacterial biomass as described herein. Examples of such edible carriers include starch, cyclodextrin, maltodextrin, methylcellulose, carbomethoxy cellulose, xanthan gum, and aqueous solutions thereof.

Yet another aspect of the present disclosure is direct to the use of the cyanobacterial biomass in the manufacture of a medicament or nutraceutical composition for use in the treatment of HBV infection or a symptom or disorder associated with, secondary to, or caused by the HBV infection. Still another aspect of the present disclosure is direct to the use of the cyanobacterial biomass in the treatment of the HBV infection or a symptom or disorder associated with, secondary to, or caused by the HBV infection. Similarly, the various cyanobacterial biomasses described above are also applicable in these aspects.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Characterization of FEM102 Strain

The chromosome DNA was extracted from the FEM102 strain. After amplification by polymerase chain reaction (PCR), the sequence of the 16S-23S rDNA was analyzed by ABI 3730 DNA Analyzer using ABI BigDye V3.1. The analysis result indicated that the 16S-23S ribosomal RNA (rRNA) gene of FEM102 strain comprises the nucleotide sequence as set forth in SEQ ID NO. 1. Sequence query using the nucleotide BLAST database provided online by Nation Center for Biotechnology Information (NCBI) indicated that this sequence is highly conserved among various *Arthrospira* spp., including *A. maxima* (also known as *Spirulina maxima*), *A. platensis* (also known as *S. platensis*), *A. erdosensis*, *A. fusiformis*, *A. indica*, and *A. terebriformis*.

Preparation of FEM102 Tablet

The FEM102 dried powder was prepared as follows. First, the FEM-102 strain (stock culture: 350 L; O.D. 0.2) was cultured in the medium as listed in Tables 1-3 (350,000 L) at 25 to 32° C. for 20 to 28 days. The biomass was collected using a 50-μm filter and then washed with clean water 5 times so as to reduce the salt content and other contaminants of the biomass. After the filtration using the 50-μm filter, the biomass was centrifuged to remove the water content (<95% by weight), and the precipitate was spray dried. Approximately 350,000 liters cultivation gave rise to about 120 to 180 kg of FEM102 powder. As could be appreciated by persons having ordinary skill in the art, the contents of the culture medium, as described herein, are provided for illustration purposes only, and should not be construed as a limitation to the scope of the present invention. Rather, persons having ordinary skill in the art may adjust or modify the culture medium as they see fit.

The FEM102 powder was then mixed with silicon dioxide or the sucrose ester of fatty acid, and pressed to form tablets (hereafter, the "FEM102 tablets"), in which each FEM102 tablet (500 mg) comprised 495 mg of FEM-102 strain and 5 mg of silicon dioxide/sucrose ester of fatty acid.

TABLE 1

Ingredients of culture medium

| Ingredients | Amount for final 1 L |
|---|---|
| NaHCO$_3$ | 13.61 g |
| Na$_2$CO$_3$ | 4.03 g |
| K$_2$HPO$_4$ | 0.5 g |
| NaNO$_3$ | 2.5 g |
| K$_2$SO$_4$ | 1 g |
| NaCl | 1 g |
| MgSO$_4$•7H$_2$O | 0.2 g |
| CaCl$_2$•2H$_2$O | 0.04 g |
| FeSO$_4$•4H$_2$O | 0.01 g |

TABLE 1-continued

Ingredients of culture medium

| Ingredients | Amount for final 1 L |
|---|---|
| A5 metal stock* | 6 ml |
| Micronutrient solution** | 1 ml |

*The ingredients of A5 metal stock were summarized in Table 2.
**The ingredients of Micronutrient solution were summarized in Table

TABLE 2

Ingredients of A5 metal stock

| Ingredients | Amount for final 1 L |
|---|---|
| Na$_2$EDTA•2H$_2$O | 0.75 g |
| FeCl$_3$•6H$_2$O | 0.097 g |
| MnCl$_2$•4H$_2$O | 0.041 g |
| ZnCl$_2$ | 0.005 g |
| CoCl$_2$•6H$_2$O | 0.002 g |
| Na$_2$MoO$_4$•2H$_2$O | 0.004 g |

TABLE 3

Ingredients of micronutrient solution

| Ingredients | Amount for final 1 L |
|---|---|
| CuSO$_4$•5H$_2$O | 0.02 g |
| ZnSO$_4$•7H$_2$O | 0.044 g |
| CoCl$_2$•6H$_2$O | 0.002 g |
| MnCl$_2$•4H$_2$O | 0.012 g |
| Na$_2$MoO$_4$•2H$_2$O | 0.012 g |
| H$_3$BO$_3$ | 0.62 g |
| Na$_2$EDTA•2H$_2$O | 0.05 g |

Clinical Trial

A single-center, randomized, open-label clinical trial was designed to determine if the co-administration of the cyanobacterial biomass and the antiviral agent could reduce the sera level of HBsAg detectable in patients suffering from chronic HBV infection. The protocol of the clinical trial and the consent form were approved by the Internal Review Board of Taipei Municipal Wanfang Hospital.

Patient inclusion criteria include age between 20 to 75 years, males and females; patients with documented chronic hepatitis B and had been taking any of the oral antiviral drugs of Entecavir, Telbivudine, and Tenofovir for at least one year; and the HBV DNA level was less than 20 IU/mL. Patients allergic to seafood were excluded from the trial.

A total of 350 patients were evaluated for eligibility; 247 were excluded and 43 were declined to participate. Sixty (60) patients meeting the inclusion and exclusion criteria and who have signed informed consent forms will be randomized to receive antiviral agent (20, Control group), antiviral agent plus 3 grams of FEM102 tablet (20, Low-dose group), or antiviral agent plus 6 grams of FEM102 tablet (20, High-dose group) on a daily basis for at least 6 months. The liver and kidney functions, levels of qHBsAg, HBeAg, B12, and steatosis/fibrosis were investigated at the beginning and the 1$^{st}$, 3$^{rd}$ and 6$^{th}$ month. Rank-sum test was used for statistical analysis. The patient demographics and baseline characteristics were listed in the Table 4.

TABLE 4

Patient demographics and baseline characteristics

| | Control (n = 20) | Low-dose (3 g/d of FEM-102) (n = 20) | High-dose (6 g/d of FEM-102) (n = 20) | P value |
|---|---|---|---|---|
| Age (years) | 49.5 ± 12.33 | 49.84 ± 10.395 | 53.79 ± 10.718 | 0.153 |
| Male | 15 (75%) | 13 (65%) | 15 (75%) | 0.72 |
| Female | 5 (25%) | 7 (35%) | 5 (25%) | |
| ALT (IU/L) | 38.39 ± 54.504 | 32.26 ± 26.066 | 30 ± 24.792 | 0.962 |
| qHBsAg (IU/mL) | 1805 ± 3214.7 | 1084 ± 1520.2 | 1008 ± 1439.5 | 0.677 |
| Fibrosis (kPa) | 7.83 ± 3.949 | 8.185 ± 5.931 | 8.22 ± 3.193 | 0.416 |
| Steatosis (dB/m) | 261.8 ± 54.812 | 275.8 ± 68.092 | 260.6 ± 57.962 | 0.681 |
| Positive HBeAg (n) | 7 (35%) | 5 (25%) | 2 (10%) | 0.207 |

As could be seen in Table 4, there were no significant differences among the control, low-dose and high-dose groups regarding the age, sex, ALT (alanine aminotransferase), level of quantitative HBsAg, HBeAg status, and severity of fibrosis and steatosis at the beginning of the trial.

In particular, patients assigned to each group was treated with their respective original antiviral agent at the recommended dosage: Entecavir (500 mg/tab; one tab per day), Telbivudine (600 mg/tab; one tab per day) or Tenofovir (300 mg/tab; one tab per day). As to patients assigned to the low-dose and high-dose groups, 6 FEM102 500 mg tablets and 12 FEM102 500 mg tablets were also administered three times a day. Specifically, the patients in the low-dose group took two tablets before each meal, and the patients in the high-dose group took four tablets before each meal.

During the trial, twelve patients in the control group discontinued the intervention, and the low-dose and high-dose group each had four and eight patients who discontinued the intervention.

Results: Biological Effect of FEM102 Tablet

One, three and six months after the first administration, the blood samples of patients in each group were analyzed by enzyme-linked immunosorbent assay (ELISA) to determine the levels of HBsAg. The qHBsAg level changes (each patient's qHBsAg level measured at a given time point minus the patient's qHBsAg level measured at the beginning of the trial) for each group were summarized in FIG. 1 and Table 5.

The data provided in FIG. 1 and Table 5 indicated that the level of qHBsAg changed in a dose-dependent manner in patients treated with FEM102 tablets, as compared with those of the control group. A significant difference was observed between the high-dose group and the control group at month 1, 3, and 6.

TABLE 5

Effect of FEM102 tablet on HBsAg level

| Group | Month | Mean qHBsAg change | Standard deviation |
|---|---|---|---|
| Control | 0 | 0 | 0 |
| Low-dose | 0 | 0 | 0 |
| High-dose | 0 | 0 | 0 |
| Control | 1 | 56.56 | 121.52 |
| Low-dose | 1 | 4.31 | 59.60 |
| High-dose | 1 | −32.00 | 53.74 |
| Control | 3 | 52.02 | 131.83 |
| Low-dose | 3 | −26.56 | 33.71 |
| High-dose | 3 | −30.38 | 53.23 |
| Control | 6 | −16.68 | 121.63 |
| Low-dose | 6 | −24.58 | 96.28 |
| High-dose | 6 | −68.96 | 136.14 |

Figure 2:
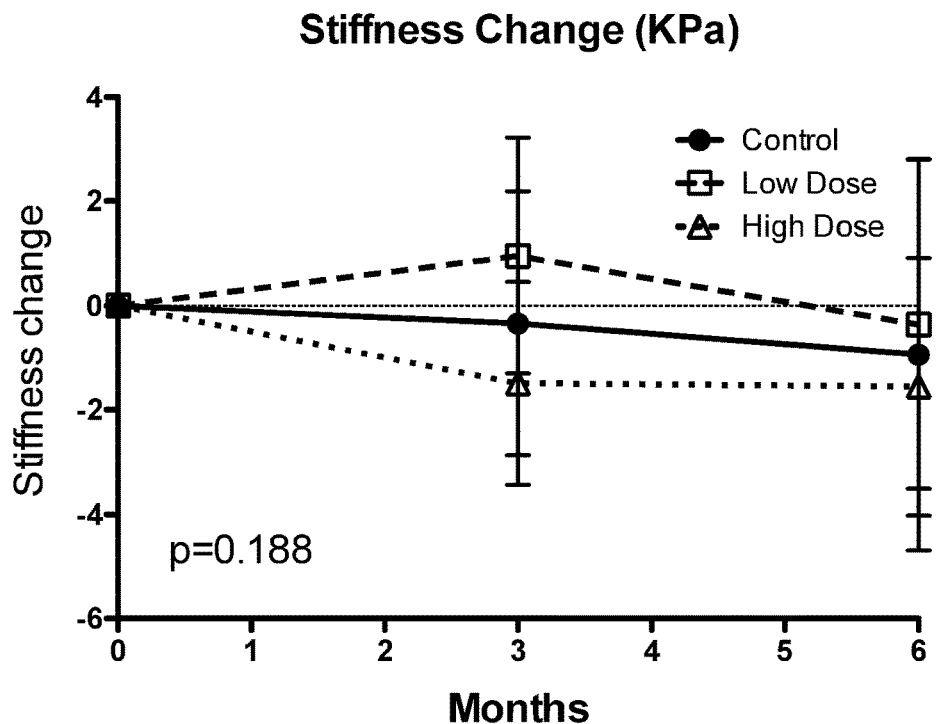
FIG. 2 is the data depicting the liver stiffness changes of subjects treated with specified treatments.

The liver stiffness in the patients was evaluated by Fibroscan®, a non-invasive device for the assessment of fibrosis and steatosis, and results are summarized in FIG. 2 and Table 6. The Fibroscan value (FS) may serve as an indicator of the severity of liver fibrosis. In general, an FS value higher than 7.0 kPa indicates that the patient has a significant fibrosis; an FS value higher than 9.1 kPa indicates that the patient has a severe fibrosis; and an FS value higher than 12.5 kPa indicates that the patient has a liver cirrhosis. The data summarized in Table 6 indicated that the co-administration of the antiviral agent (e.g., Entecavir, Telbivudine or Tenofovir) and FEM102 tablet (6 grams) significantly reduced the patients' FS value, suggesting an improvement of the patients' liver condition, in which liver fibrosis appeared to be less severe (7.521 KPa (6 months) v.s. 9.242 KPa (Baseline), p=0.005).

TABLE 6

Effect of FEM-102 tablet with antiviral agent for 6 months on liver stiffness

| Group | Month | Mean stiffness change | Standard deviation |
|---|---|---|---|
| Control | 0 | 0 | 0 |
| Low-dose | 0 | 0 | 0 |
| High-dose | 0 | 0 | 0 |
| Control | 3 | −0.34 | 2.53 |
| Low-dose | 3 | 0.96 | 2.26 |
| High-dose | 3 | −1.49 | 1.95 |
| Control | 6 | −0.94 | 3.75 |
| Low-dose | 6 | −0.36 | 3.16 |
| High-dose | 6 | −1.55 | 2.47 |

Taken together, the data above confirmed that the administration of a cyanobacterial biomass (e.g., the FEM102 tablet derived from dried *A. maxima*) may help clear the HBV particles and ameliorate liver fibrosis in patients having chronic HBV infection. As HBV particles and liver fibrosis have been regarded as factors causing disturbed sleep pattern or insomnia in these patients, we further evaluated whether 'the FEM102 tablet could improve the sleep quality of such patients.

The sleep quality was assessed and scored in accordance with several sleep-related parameters, including the time taken to fall asleep, duration of wakeups during sleep time, total sleeping time, and mental performance during the day (such as memory, cognition, and attention performance) etc. The score was inversely proportional to the sleep quality; in other words, the poorer the sleep quality, the higher the score was assessed. Results are summarized in Table 7.

The data of Table 7 indicated that the sleep quality of patients co-treated with the antiviral agent and the FEM102 tablet was obviously better than that of patients treated with the antiviral agent alone.

TABLE 7

Effect of FEM102 tablet on sleep state of patients

| Group | Value of sleep state | |
|---|---|---|
| | 0 Month | 3 Month |
| Control | 3.63 ± 2.42 | 3.88 ± 3.63 |
| Low-dose | 3.19 ± 3.60 | 2.61 ± 3.73 |
| High-dose | 3.54 ± 3.23 | 2.45 ± 3.00 | the

In conclusion, the present disclosure provides a cyanobacterial biomass (e.g., the biomass derived from *A. maxima*), a pharmaceutical composition (such as, the FEM102 tablet) comprising the same, and the uses thereof in the treatment of chronic HBV infection. Specifically, the present cyanobacterial biomass is useful in reducing the HBV particles (as represented by the HBsAg level detectable in the serum of the patient) and improving the condition of liver fibrosis as well as the sleep quality of patients with chronic HBV infection.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for reducing the level of the surface antigen of hepatitis B virus (HBsAg) detectable in a subject suffering from chronic hepatitis B virus (HBV) infection in a subject in need thereof, comprising the step of administering to the subject an effective amount of a cyanobacterial biomass, and the step of administering an effective amount of an antiviral agent, wherein the cyanobacterial biomass is derived from *Arthrospira maxima* and the cyanobacterial biomass is administered orally at an effective amount of 1 to 20 grams per day for at least three months to result in a decrease of HBsAg level by at least 30%.

2. The method according to claim 1, wherein the antiviral agent is an interferon alpha (IFN-$\alpha$), pegylated IFN-$\alpha$, nucleoside analog, or nucleotide analog.

3. The method according to claim 1, wherein the antiviral agent is acyclovir, famciclovir, ganciclovir, valacyclovir, vidarabine, ribavirin, zoster-immune globulin (ZIG), lamivudine, adefovir, dipivoxil, entecavir, telbivudine, clevudine, or tenofovir.

4. The method according to claim 1, wherein the subject suffers from insomnia associated with chronic HBV infection, and the cyanobacterial biomass is administered for at least three months to mitigate insomnia.

5. The method according to claim 1, wherein the subject suffers from liver fibrosis associated with chronic HBV infection, and the cyanobacterial biomass is administered for at least three months to mitigate liver fibrosis.

6. The method according to claim 1, wherein the cyanobacterial biomass is formulated into a pharmaceutical composition that comprises the effective amount of the cyanobacterial biomass and a pharmaceutically acceptable excipient.

7. The method according to claim 6, wherein the pharmaceutical composition is formulated into a solid dosage form.

8. The method according to claim 7, wherein the pharmaceutically acceptable excipient is silicon dioxide or a sucrose ester of fatty acid.

* * * * *